United States Patent
Metcalf

(10) Patent No.: US 10,609,944 B1
(45) Date of Patent: Apr. 7, 2020

(54) COMPOSITIONS COMPRISING 2-[(1R,6R)-6-ISOPROPENYL-3-METHYLCYCLOHEX-2-EN-1-YL]-3-HYDROXY-5-PENTYLPHENOLATE AND 2-[(1R,6R)-6-ISOPROPENYL-3-METHYLCYCLOHEX-2-EN-1-YL]-5-PENTYLBENZENE-1,3-DIOL

(71) Applicant: Natural Extraction Systems, LLC, Boulder, CO (US)

(72) Inventor: Douglas G. Metcalf, Broomfield, CO (US)

(73) Assignee: Natural Extraction Systems, LLC, Boulder, CO (US)

( * ) Notice: Subject to any disclaimer, the term of this patent is extended or adjusted under 35 U.S.C. 154(b) by 0 days.

(21) Appl. No.: 16/239,463

(22) Filed: Jan. 3, 2019

Related U.S. Application Data

(60) Provisional application No. 62/787,717, filed on Jan. 2, 2019, provisional application No. 62/780,169, filed on Dec. 14, 2018.

(51) Int. Cl.
| | |
|---|---|
| *A23L 33/105* | (2016.01) |
| *A23L 2/52* | (2006.01) |
| *A61K 36/185* | (2006.01) |
| *A23L 29/00* | (2016.01) |
| *C07C 39/19* | (2006.01) |

(52) U.S. Cl.
CPC ............ *A23L 33/105* (2016.08); *A23L 2/52* (2013.01); *A23L 29/035* (2016.08); *A61K 36/185* (2013.01); *A23V 2002/00* (2013.01); *A23V 2250/2132* (2013.01)

(58) Field of Classification Search
None
See application file for complete search history.

(56) References Cited

U.S. PATENT DOCUMENTS

| | | |
|---|---|---|
| 9,907,823 B1 | 3/2018 | Kuhrts |
| 2009/0044700 A1 | 2/2009 | Dietlin et al. |
| 2014/0263467 A1 | 9/2014 | Wardle et al. |
| 2016/0018424 A1* | 1/2016 | Lucas ............... G01N 33/52 436/93 |
| 2017/0246897 A1 | 8/2017 | Brehm et al. |
| 2018/0169035 A1 | 6/2018 | Eyal |
| 2019/0030170 A1* | 1/2019 | Kingsley ............. A61K 47/40 |

FOREIGN PATENT DOCUMENTS

WO  WO-2018/183115 A1  10/2018

OTHER PUBLICATIONS

Mechoulam, et al., Tetrahedron, 24:5615. (Year: 1968).*
Kogan, et al., J. Med. Chem., 47:3800. (Year: 2004).*
U.S. Appl. No. 16/440,878, filed Jun. 2019, Metcalf; Douglas.*
U.S. Appl. No. 16/440,889, filed Jun. 2019, Metcalf; Douglas.*
Mazina et al., "A rapid capillary electrophoresis method with LED-induced native fluorescence detection for the analysis of cannabinoids in oral fluid," Anal Methods, 7:7741-7747 (2015).
Dow Corning, "Corning Plastic Storage Bottles Product Selection Guide," 1-8 (2016).
Martijn, "CBD Products According to Sensi Seeds," 1-12 (2016).
Wilson et al., "HU-331 and Oxidized Cannabidiol Act as Inhibitors of Human Topoisomerase IIα and β," Chemical Research in Toxicology, 31:137-144 (2018).

\* cited by examiner

*Primary Examiner* — Michael Barker
(74) *Attorney, Agent, or Firm* — Foley Hoag LLP; David P. Halstead; Laura A. Wzorek

(57) ABSTRACT

Various aspects of the disclosure relate to compositions comprising 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol.

18 Claims, 1 Drawing Sheet

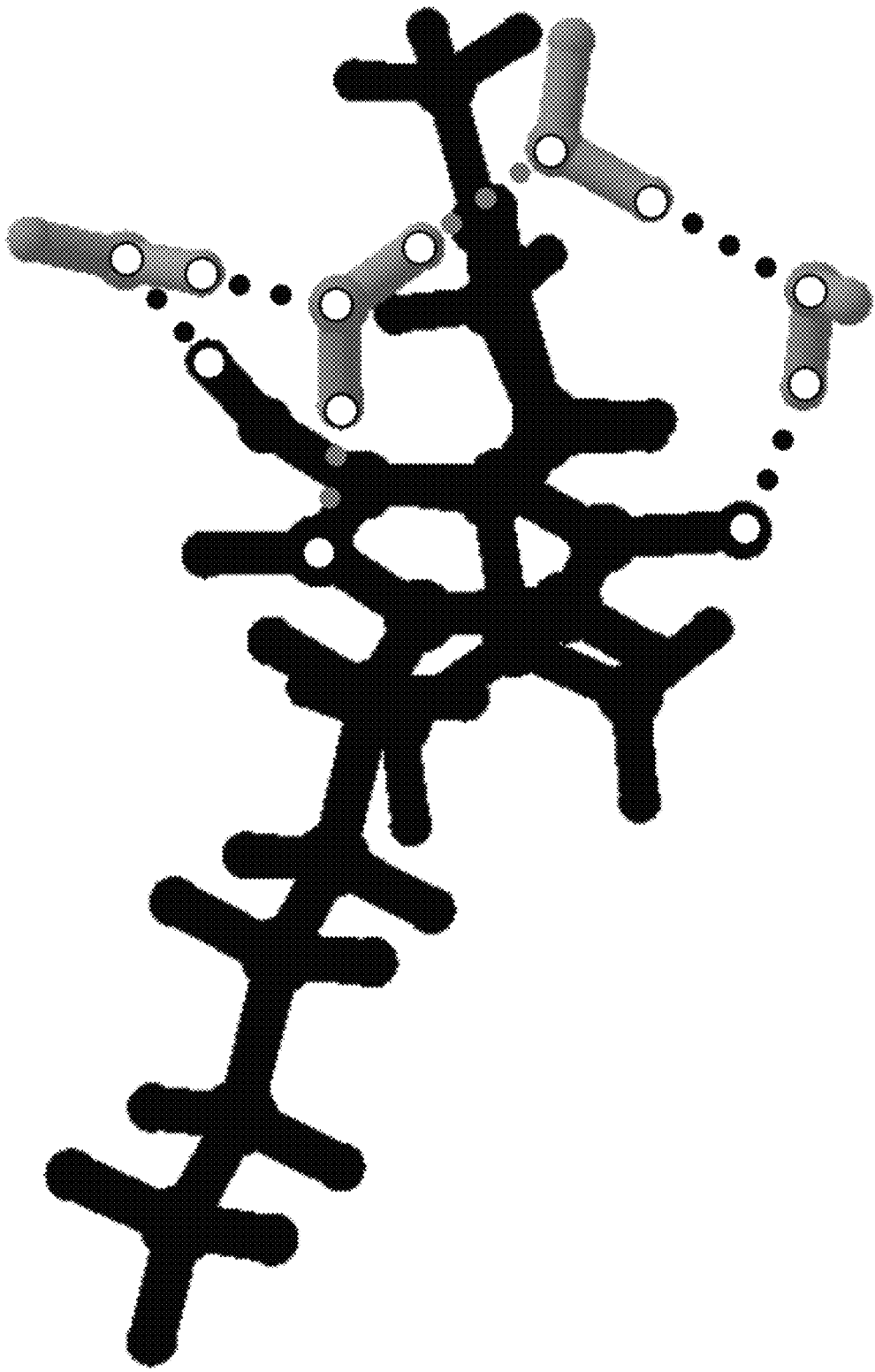

COMPOSITIONS COMPRISING 2-[(1R,6R)-6-ISOPROPENYL-3-METHYLCYCLOHEX-2-EN-1-YL]-3-HYDROXY-5-PENTYLPHENOLATE AND 2-[(1R,6R)-6-ISOPROPENYL-3-METHYLCYCLOHEX-2-EN-1-YL]-5-PENTYLBENZENE-1,3-DIOL

PRIORITY CLAIM

This patent document claims priority to U.S. Provisional Patent Application No. 62/780,169, filed Dec. 14, 2018, and U.S. Provisional Patent Application No. 62/787,717, filed Jan. 2, 2019, each of which is incorporated by reference in its entirety.

BACKGROUND

The *Cannabis* plant produces cannabidiolic acid, which displays only nominal pharmacological activity. Cannabidiolic acid can be converted into cannabidiol, which displays robust pharmacological activity, by heating cannabidiolic acid under vacuum.

Cannabidiol is sparingly soluble in water. Attempts have been made to improve the solubility of cannabidiol to produce beverages suitable for human consumption, for example, by emulsification. Thermostable emulsions of cannabidiol frequently display unfavorable characteristics including undesirable taste. Improved methods of solubilizing cannabidiol are desirable to produce beverages comprising cannabidiol.

BRIEF DESCRIPTION

Various aspects of the disclosure relate to a composition comprising 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1:10 to 1,000,000:1.

In some embodiments, a composition is a liquid.

In some embodiments, a composition has a pH, and the pH of the composition is 7 to 13. In some specific embodiments, the pH of a composition is 8 to 10.

In some specific embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1:1 to 100:1. In some specific embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 10:1 to 1,000:1. In some specific embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 100:1 to 10,000:1. In some specific embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1,000:1 to 100,000:1. In some specific embodiments, a composition comprises 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 10,000:1 to 1,000,000:1.

In some embodiments, a composition comprises water. In specific embodiments, a composition comprises water at a concentration by weight of 50% to 99.999%. In more specific embodiments, a composition comprises water at a concentration by weight of 80% to 99.99%.

In some embodiments, a composition comprises ethanol. In some specific embodiments, a composition comprises ethanol at a concentration by weight of 50 parts per million to 2%. In some specific embodiments, a composition comprises ethanol at a concentration by weight of 1% to 20%. In some specific embodiments, a composition comprises ethanol at a concentration by weight of 10% to 99%.

In some specific embodiments, a composition comprises 2-[(1R,6R)-6-isopropenyl-3-methylcyclohex-2-en-1-yl]-3-hydroxy-5-pentylphenolate at a concentration of 1 milligram per liter to 100 milligrams per liter. In some specific embodiments, a composition comprises 2-[(1R,6R)-6-isopropenyl-3-methylcyclohex-2-en-1-yl]-3-hydroxy-5-pentylphenolate at a concentration of 50 milligrams per liter to 5 grams per liter. In some specific embodiments, a composition comprises 2-[(1R,6R)-6-isopropenyl-3-methylcyclohex-2-en-1-yl]-3-hydroxy-5-pentylphenolate at a concentration of 2 grams per liter to 200 grams per liter.

In some embodiments, a composition comprises one or more of sodium ion ($Na^+$), potassium ion ($K^+$), calcium ion ($Ca^{2+}$), magnesium ion ($Mg^{2+}$), chloride ion ($Cl^-$), sulfate ($SO_4^{2-}$), bicarbonate ($HCO_3^-$), and carbonate ($CO_3^{2-}$).

In some embodiments, a composition comprises one or more of caffeine, thiamine, niacin, nicotinamide, riboflavin, pantothenate, sucrose, fructose, glucose, acesulfame, saccharin, stevioside, rebaudioside A, sucralose, tagatose, erythritol, maltitol, xylitol, mannitol, isomalt, and a mogroside.

In some embodiments, a composition comprises a solid phase, the solid phase comprises a salt, and the salt comprises 2-[(1R,6R)-6-isopropenyl-3-methylcyclohex-2-en-1-yl]-3-hydroxy-5-pentylphenolate. In specific embodiments, a salt comprises a cation selected from sodium ion ($Na^+$), potassium ion ($K^+$), calcium ion ($Ca^{2+}$), and magnesium ion ($Mg^{2+}$).

Various aspects of the disclosure relate to a container comprising a sealed chamber and a composition according to any of the embodiments of the present disclosure disposed within the sealed chamber.

BRIEF DESCRIPTION OF THE DRAWINGS

FIG. 1 is a model of 2-[(1R,6R)-6-isopropenyl-3-methylcyclohex-2-en-1-yl]-3-hydroxy-5-pentylphenolate (black) bound to four water molecules (grey). Six hydrogen bonds are depicted with dotted lines.

DETAILED DESCRIPTION

Various aspects of the disclosure relate to the discovery that 2-[(1R,6R)-6-isopropenyl-3-methylcyclohex-2-en-1-yl]-3-hydroxy-5-pentylphenolate is stable in water at a pH of less than 9.5. This discovery was unexpected and surprising because the $pK_a$ of 2-[(1R,6R)-6-isopropenyl-3-methylcyclohex-2-en-1-yl]-5-pentylbenzene-1,3-diol ("1R,6R CBD"), which is the conjugate acid of 2-[(1R,6R)-6-isopropenyl-3-methylcyclohex-2-en-1-yl]-3-hydroxy-5-pentylphenolate, was previously determined to be greater than 9 and also because 1R,6R CBD lacks appreciable solubility in water. Based on this information, the beverage and nutritional supplement industries overlooked attempts to solubilize 1R,6R CBD under alkaline conditions. The present disclosure reveals that 2-[(1R,6R)-6-isopropenyl-3-methylcyclohex-2-en-1-yl]-3-hydroxy-5-pentylphenolate is soluble and stable in water at pH ranges below 10. The ramifications of this discovery include the development of commercially-viable beverages that comprise 2-[(1R,6R)-6-isopropenyl-3-methylcyclohex-2-en-1-yl]-3-hydroxy-5-pentylphenolate.

Various aspects of the disclosure relate to 2-[(1R,6R)-6-isopropenyl-3-methylcyclohex-2-en-1-yl]-3-hydroxy-5-pentylphenolate and compositions comprising 2-[(1R,6R)-6-isopropenyl-3-methylcyclohex-2-en-1-yl]-3-hydroxy-5-pentylphenolate.

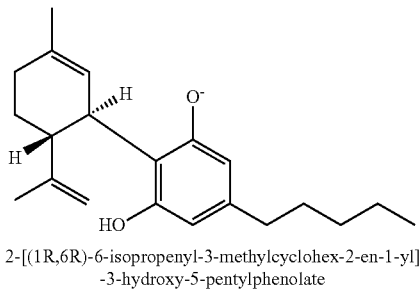 [SMILES: C=C(C)[C@@H]1CCC(C)=C[C@H]1c1c([O-])cc(CCCCC)cc1O]

2-[(1R,6R)-6-isopropenyl-3-methylcyclohex-2-en-1-yl]
-3-hydroxy-5-pentylphenolate In some embodiments, a composition comprises a salt of 2-[(1R,6R)-6-isopropenyl-3-methylcyclohex-2-en-1-yl]-3-hydroxy-5-pentylphenolate. The salt can be, for example, a sodium salt, potassium salt, calcium salt, or magnesium salt.

In some embodiments, a composition comprises 1R,6R CBD.

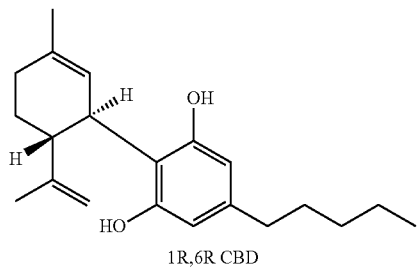 [SMILES: C=C(C)[C@@H]1CCC(C)=C[C@H]1c1c(O)cc(CCCCC)cc1O]

1R,6R CBD

In some embodiments, a composition lacks chlorophyll, cellulose, or both chlorophyll and cellulose.

In some embodiments, a composition comprises 2-[(1R,6R)-6-isopropenyl-3-methylcyclohex-2-en-1-yl]-3-hydroxy-5-pentylphenolate at a concentration of 5 parts per million ("ppm") to 10% by weight. In some embodiments, a composition comprises 2-[(1R,6R)-6-isopropenyl-3-methylcyclohex-2-en-1-yl]-3-hydroxy-5-pentylphenolate at a concentration of 5% to 97% by weight.

In some embodiments, a composition further comprises water, ethanol, or both water and ethanol.

In some embodiments, a composition comprises water at a concentration by weight of at least 10%. In some embodiments, a composition comprises water at a concentration by weight of 10% to 99.999%.

In some embodiments, a composition comprises ethanol at a concentration by weight of at least 10 parts per trillion ("ppt") such as at least 10 parts per billion ("ppb"). In some embodiments, a composition comprises ethanol at a concentration by weight of 10 ppt to 0.5%.

In some embodiments, a composition comprises ethanol at a concentration by weight of at least 0.1%. In some embodiments, a composition comprises ethanol at a concentration by weight of 0.1% to 1%, 0.5% to 5%, 1% to 10%, or 5% to 15%.

In some embodiments, a composition comprises ethanol at a concentration by weight of at least 10%. A composition can comprise ethanol at a concentration by weight of 10% to 99.9%.

In some embodiments, a composition comprises sodium ion at a concentration by weight of at least 10 ppb. A composition can optionally comprise sodium ion at a concentration by weight of 10 ppb to 10%.

In some embodiments, a composition comprises potassium ion at a concentration by weight of at least 10 ppb. A composition can optionally comprise potassium ion at a concentration by weight of 10 ppb to 10%.

In some embodiments, a composition comprises sodium ion and potassium ion at a total concentration by weight of at least 10 ppb. A composition can optionally comprise sodium ion and potassium ion at a total concentration by weight of 10 ppb to 10%.

In some embodiments, a composition further comprises sucrose, fructose, glucose, acesulfame, aspartame, saccharin, stevia, sucralose, tagatose, neotame, sorbitol, xylitol, erythritol, maltitol, mannitol, isomalt, or lactitol.

In some embodiments, a composition has a pH of 7 to 14, 7 to 12, 8 to 12, 9 to 12, 10 to 12, 11 to 12, 7 to 11, 8 to 11, 9 to 11, 10 to 11, 7 to 9, 8 to 10, 9 to 11, 10 to 12, 11 to 13, 12 to 14, 7 to 8, 7.5 to 8.5, 8 to 9, 8.5 to 9.5, 9 to 10, 9.5 to 10.5, 10 to 11, 10.5 to 11.5, 11 to 12, 11.5 to 12.5, 12 to 13, 12.5 to 13.5, or 13 to 14.

In some embodiments, a composition further comprises carbonate, bicarbonate, or both carbonate and bicarbonate. For example, a composition can comprise carbonate and bicarbonate at a total concentration by weight of at least 10 ppb. A composition can optionally comprise carbonate and bicarbonate at a total concentration by weight of 10 ppb to 10%.

Various aspects of the present disclosure relate to a sealed container comprising a composition described anywhere in the present disclosure. In some embodiments, the sealed container is a glass bottle, aluminum can (which optionally comprises a polymer liner disposed within the aluminum can), or a plastic bottle. A sealed container can be, for example, a barrel, jar, can, bottle, box, pouch, or molded plastic. A sealed container typically comprises a sealed chamber in which a composition according to the present disclosure is disposed.

A sealed container can optionally be sealed with a cap such as a screw cap.

In some embodiments, a container comprises at least 1 milligram ("mg") of a composition described in the present disclosure. In some embodiments, a container comprises 1 mg to 1000 kg of a composition described in the present disclosure.

In some embodiments, a container comprises at least 1 microliter of a composition described in the present disclosure. In some embodiments, a container comprises 1 microliter to 1000 L of a composition described in the present disclosure.

In some embodiments, a composition is suitable for human consumption. In some embodiments, a composition is a beverage.

Numerous combinations of the features described in the present disclosure are possible, and the inventors contemplate each possible combination of features as would be apparent to one of ordinary skill in the relevant arts at the Dec. 14, 2018 priority date of this patent document. The words "comprise," "comprising," and their alternate forms refer to open sets to which additional features can optionally be added. The following exemplification section discloses specific embodiments that fall within the scope of the preceding description, and the examples set forth in the exemplification section do not limit the present disclosure or following claims in any way.

EXEMPLIFICATION

Example 1. Preparation of 2-[(1R,6R)-6-isopropenyl-3-methylcyclohex-2-en-1-yl]-3-hydroxy-5-pentylphenolate 0.5 grams of 1R,6R CBD was dissolved in 3.3 milliliters 0.5 molar potassium hydroxide (0.5 M KOH) in ethanol to produce 2-[(1R,6R)-6-isopropenyl-3-methylcyclohex-2-en-1-yl]-3-hydroxy-5-pentylphenolate. The conversion of 1R,6R CBD to 2-[(1R,6R)-6-isopropenyl-3-methylcyclohex-2-en-1-yl]-3-hydroxy-5-pentylphenolate was readily confirmed by color because 1R,6R CBD has a yellow-brown color and 2-[(1R,6R)-6-isopropenyl-3-methylcyclohex-2-en-1-yl]-3-hydroxy-5-pentylphenolate has a deep purple color.

The 2-[(1R,6R)-6-isopropenyl-3-methylcyclohex-2-en-1-yl]-3-hydroxy-5-pentylphenolate was diluted with 26.7 milliliters of 0.1 molar sodium carbonate (0.1 M $Na_2CO_3$) and divided into three aliquots of 10 milliliters each, each aliquot containing approximately:

167 milligrams 2-[(1R,6R)-6-isopropenyl-3-methylcyclohex-2-en-1-yl]-3-hydroxy-5-pentylphenolate
21 milligrams potassium ion
41 milligrams sodium ion
53 milligrams carbonate
868 milligrams ethanol
8.8 grams water Example 2. Preparation of Salts Comprising 2-[(1R,6R)-6-isopropenyl-3-methylcyclohex-2-en-1-yl]-3-hydroxy-5-pentylphenolate A first aliquot from Example 1 was lyophilized to produce salts including a potassium 2-[(1R,6R)-6-isopropenyl-3-methylcyclohex-2-en-1-yl]-3-hydroxy-5-pentylphenolate salt and a sodium 2-[(1R,6R)-6-isopropenyl-3-methylcyclohex-2-en-1-yl]-3-hydroxy-5-pentylphenolate salt.

Example 3. Reconstituting 1R,6R CBD 0.1 milliliters of 5 molar citric acid (5 M citric acid) was added to a second aliquot from Example 1 to reconstitute 1R,6R CBD from 2-[(1R,6R)-6-isopropenyl-3-methylcyclohex-2-en-1-yl]-3-hydroxy-5-pentylphenolate. The reconstitution of 1R,6R CBD was confirmed by color.

Example 4. Determining pH Stability of 2-[(1R,6R)-6-isopropenyl-3-methylcyclohex-2-en-1-yl]-3-hydroxy-5-pentylphenolate in Water Various acid dissociation constants ($K_a$) for the 1R,6R CBD hydroxyl protons have been reported, and the corresponding $pK_a$'s (which are the negative $\log_{10}$'s of the acid dissociation constants) range from 9.13 to 9.64. This data suggests that 2-[(1R,6R)-6-isopropenyl-3-methylcyclohex-2-en-1-yl]-3-hydroxy-5-pentylphenolate is not viable for inclusion in beverages. If the $pK_a$ of 1R,6R CBD were 9.13, for example, then 1R,6R CBD might be expected to lack stability at a pH of 9.5 because approximately 30% of the dissolved 2-[(1R,6R)-6-isopropenyl-3-methylcyclohex-2-en-1-yl]-3-hydroxy-5-pentylphenolate and 1R,6R CBD would exist as 1R,6R CBD, which might form a lipid phase. This lipid phase would be a thermodynamic sink if the lipid phase were to separate from the aqueous phase. Le Châtelier's principle could drive the conversion of 2-[(1R,6R)-6-isopropenyl-3-methylcyclohex-2-en-1-yl]-3-hydroxy-5-pentylphenolate to 1R,6R CBD until the composition existed as an aqueous phase essentially devoid of 2-[(1R,6R)-6-isopropenyl-3-methylcyclohex-2-en-1-yl]-3-hydroxy-5-pentylphenolate and a lipid phase comprising 1R,6R CBD. A greater $pK_a$, such as a $pK_a$ of 9.64, would magnify this detrimental effect. Beverages having a pH above 9.5 to 10 are uncommon because they risk causticity.

Experiments were nevertheless performed to determine whether 2-[(1R,6R)-6-isopropenyl-3-methylcyclohex-2-en-1-yl]-3-hydroxy-5-pentylphenolate could be stabilized in aqueous solution. 1 gram of 1R,6R CBD was dissolved in 6.6 milliliters of 0.5 molar potassium hydroxide (0.5 M KOH) in ethanol to produce 2-[(1R,6R)-6-isopropenyl-3-methylcyclohex-2-en-1-yl]-3-hydroxy-5-pentylphenolate. The solution was then diluted with 100 millimolar sodium carbonate (100 mM $Na_2CO_3$) in water to a final volume of 50 milliliters and to a 2-[(1R,6R)-6-isopropenyl-3-methylcyclohex-2-en-1-yl]-3-hydroxy-5-pentylphenolate concentration of approximately 20 grams per liter. 0.5 milliliters of the 2-[(1R,6R)-6-isopropenyl-3-methylcyclohex-2-en-1-yl]-3-hydroxy-5-pentylphenolate solution was added to each of 25 test tubes containing 9.5 milliliters of 0.1 molar carbonate/bicarbonate ($CO_3^{2-}/HCO_3^-$) buffer according to Table 1. Each test tube contained approximately 10 milligrams of 2-[(1R,6R)-6-isopropenyl-3-methylcyclohex-2-en-1-yl]-3-hydroxy-5-pentylphenolate at a concentration of approximately 1 gram per liter, approximately 0.66% ethanol by weight, trace potassium ion, and variable sodium ion, carbonate ion, and bicarbonate ion. pH's were confirmed by multiple different measurements.

TABLE 1

Aqueous compositions comprising 2-[(1R,6R)-6-isopropenyl-3-methylcyclohex-2-en-1-yl]-3-hydroxy-5-pentylphenolate at variable pH

| Sample | pH | 0.1M $Na_2CO_3$* | 0.1M $NaHCO_3$ |
|---|---|---|---|
| 1 | 9.1 | 0.06 mL | 8.94 mL |
| 2 | 9.2 | 0.20 mL | 8.80 mL |
| 3 | 9.3 | 0.36 mL | 8.64 mL |
| 4 | 9.4 | 0.56 mL | 8.44 mL |
| 5 | 9.5 | 0.80 mL | 8.20 mL |
| 6 | 9.6 | 1.08 mL | 7.92 mL |
| 7 | 9.7 | 1.41 mL | 7.59 mL |
| 8 | 9.8 | 1.78 mL | 7.22 mL |
| 9 | 9.9 | 2.21 mL | 6.79 mL |
| 10 | 10.0 | 2.67 mL | 6.33 mL |
| 11 | 10.3 | 4.25 mL | 4.75 mL |
| 12 | 10.3 | 4.25 mL | 4.75 mL |
| 13 | 10.3 | 4.25 mL | 4.75 mL |
| 14 | 10.4 | 4.79 mL | 4.21 mL |
| 15 | 10.4 | 4.79 mL | 4.21 mL |
| 16 | 10.4 | 4.79 mL | 4.21 mL |
| 17 | 10.5 | 5.32 mL | 3.68 mL |
| 18 | 10.5 | 5.32 mL | 3.68 mL |
| 19 | 10.5 | 5.32 mL | 3.68 mL |
| 20 | 11.0 | 7.42 mL | 1.58 mL |
| 21 | 11.0 | 7.42 mL | 1.58 mL |
| 22 | 11.0 | 7.42 mL | 1.58 mL |
| 23 | 11.5 | 8.44 mL | 0.56 mL |
| 24 | 11.5 | 8.44 mL | 0.56 mL |
| 25 | 11.5 | 8.44 mL | 0.56 mL |

It was expected that 2-[(1R,6R)-6-isopropenyl-3-methylcyclohex-2-en-1-yl]-3-hydroxy-5-pentylphenolate would form 1R,6R CBD at pH's below a threshold pH as evidenced by an expected color change from purple (indicative of 2-[(1R,6R)-6-isopropenyl-3-methylcyclohex-2-en-1-yl]-3-hydroxy-5-pentylphenolate) to yellow-brown (indicative of 1R,6R CBD). No color change occurred at pH's of 9.1 and above. This finding suggested that either the $pK_a$ of 1R,6R CBD is less than 9.1, at least in dilute aqueous solutions, or that it may be possible to kinetically trap 2-[(1R,6R)-6-isopropenyl-3-methylcyclohex-2-en-1-yl]-3-hydroxy-5-pentylphenolate in an aqueous solution at a pH below the $pK_a$ of 1R,6R CBD.

Example 5. Determining the Approximate $pK_a$ of 1R,6R CBD 0.5 milliliters of the 20 gram-per-liter solution of 2-[(1R,6R)-6-isopropenyl-3-methylcyclohex-2-en-1-yl]-3-hydroxy-5-pentylphenolate described in Example 4 was diluted with 9.5 milliliters of distilled water comprising varying concentrations of sodium bicarbonate, and color was monitored as shown in Table 2. pH's were confirmed by multiple different measurements.

TABLE 2

Samples used to determine an approximate $pK_a$ for 1R,6R CBD

| Sample | pH | NaHCO$_3$ concentration in millimolar | color |
|---|---|---|---|
| 26 | 8.0 | 1000 | faint purple |
| 27 | 8.3 | 500 | light purple |
| 28 | 8.6 | 250 | Purple |
| 29 | 8.9 | 125 | Purple |
| 30 | 9.2 | 62 | Purple |

A color change was visually apparent at a pH of 8.0, and a subtle color change was visually apparent at pH of 8.3. These findings suggest that the $pK_a$ of 1R,6R CBD was between 8.0 and 8.5 under the test conditions. This result is surprising given that previously reported $pK_a$'s for 1R,6R CBD range from 9.13 to 9.64 and because the chemically-related molecule resorcinol has a $pK_a$ of 9.15. Further, even though sample 26, which had a pH of 8.0, displayed a color change indicative of conversion from 2-[(1R,6R)-6-isopropenyl-3-methylcyclohex-2-en-1-yl]-3-hydroxy-5-pentylphenolate to 1R,6R CBD, no lipid phase formed, which suggests that the interconversion between 2-[(1R,6R)-6-isopropenyl-3-methylcyclohex-2-en-1-yl]-3-hydroxy-5-pentylphenolate and 1R,6R CBD in aqueous solution can kinetically trap 1R,6R CBD in the aqueous phase and inhibit the production of a lipid phase. These findings suggest that 2-[(1R,6R)-6-isopropenyl-3-methylcyclohex-2-en-1-yl]-3-hydroxy-5-pentylphenolate, the conjugate base of 1R,6R CBD, is suitable for use in beverages for human consumption.

Example 6. Confirming the Commercial Viability of Beverages Comprising 2-[(1R,6R)-6-isopropenyl-3-methylcyclohex-2-en-1-yl]-3-hydroxy-5-pentylphenolate 20 milliliters of water was removed from a 1 liter bottle of ESSENTIA® OVERACHIEVING H$_2$O®. ESSENTIA® OVERACHIEVING H$_2$O® contains purified water, sodium bicarbonate, dipotassium phosphate, magnesium sulfate, and calcium chloride, and its pH was determined to be about 9.5. The 20 milliliters of removed water was replaced with 20 milliliters of the 20 gram-per-liter solution of 2-[(1R,6R)-6-isopropenyl-3-methylcyclohex-2-en-1-yl]-3-hydroxy-5-pentylphenolate, which is described in Example 4, and the bottle was sealed using the screw-cap top of the bottle to produce a sealed container comprising approximately 400 milligrams of 2-[(1R,6R)-6-isopropenyl-3-methylcyclohex-2-en-1-yl]-3-hydroxy-5-pentylphenolate. The pH of the liquid was measured and determined to be about 10. The liquid was purple and transparent.

5 milliliters of water was removed from a 500 milliliter bottle of DASANI® purified water. DANSANI® purified water contains purified water, magnesium sulfate, potassium chloride, and sodium chloride, and its pH was determined to be about 7.0. The 5 milliliters of removed water was replaced with 5 milliliters of the 20 gram-per-liter solution of 2-[(1R,6R)-6-isopropenyl-3-methylcyclohex-2-en-1-yl]-3-hydroxy-5-pentylphenolate, which is described in Example 4, and the bottle was sealed using the screw-cap top of the bottle to produce a sealed container comprising approximately 100 milligrams of 2-[(1R,6R)-6-isopropenyl-3-methylcyclohex-2-en-1-yl]-3-hydroxy-5-pentylphenolate. The pH of the liquid was measured and determined to be about 9.5. The liquid was transparent and purple. The liquid had a faint taste similar to the taste of products comprising 1R,6R CBD in unflavored carriers.

0.5 milliliters of water was removed from a 500 milliliter bottle of DASANI® purified water. The 0.5 milliliters of removed water was replaced with 0.5 milliliters of the 20 gram-per-liter solution of 2-[(1R,6R)-6-isopropenyl-3-methylcyclohex-2-en-1-yl]-3-hydroxy-5-pentylphenolate, which is described in Example 4, and the bottle was sealed using the screw-cap top of the bottle to produce sealed container comprising approximately 10 milligrams of 2-[(1R,6R)-6-isopropenyl-3-methylcyclohex-2-en-1-yl]-3-hydroxy-5-pentylphenolate. The pH of the liquid was measured and determined to be about 8.5. The liquid was transparent and lacked discernable color.

The preceding experiments confirm that 2-[(1R,6R)-6-isopropenyl-3-methylcyclohex-2-en-1-yl]-3-hydroxy-5-pentylphenolate is suitable for use in beverages.

Example 7. Molecular Model of 2-[(1R,6R)-6-isopropenyl-3-methylcyclohex-2-en-1-yl]-3-hydroxy-5-pentylphenolate 2-[(1R,6R)-6-isopropenyl-3-methyl cyclohex-2-en-1-yl]-3-hydroxy-5-pentylphenolate was modeled to identify molecular features that might result in a lower $pK_a$ than resorcinol and other related molecules. Two water molecules are capable of hydrogen bonding with the 1-oxide oxygen of 2-[(1R,6R)-6-isopropenyl-3-methylcyclohex-2-en-1-yl]-3-hydroxy-5-pentylphenolate and the pi cloud of its 4-carbon, which carries a partial negative charge from its keto-resonance structures (FIG. 1, fourth and second grey water molecules from the left, respectively). These two water molecules can hydrogen-bond with a third water molecule (FIG. 1, third grey water molecule from the left) with bond lengths and bond geometries that are nearly identical to those found in ice, which indicates a strong likelihood of stable coordination of water by 2-[(1R,6R)-6-isopropenyl-3-methylcyclohex-2-en-1-yl]-3-hydroxy-5-pentylphenolate. The oxygen atom of the third water molecule would be about 3.0 to 3.5 angstroms away from the 2-carbon of the cyclohexenyl group, and the 2-proton would be nearly in-line with the line connecting the water oxygen and the 2-carbon, which suggests a favorable interaction similar to a hydrogen bond (not shown). A fourth water molecule (FIG. 1, first grey water molecule from the left) can connect the three other waters to the 3-hydroxyl of 2-[(1R,6R)-6-isopropenyl-3-methylcyclohex-2-en-1-yl]-3-hydroxy-5-pentylphenolate by forming two additional hydrogen bonds.

FIG. 1 shows that four coordinated water molecules can directly connect the 1-oxide of 2-[(1R,6R)-6-isopropenyl-3-methylcyclohex-2-en-1-yl]-3-hydroxy-5-pentylphenolate with its 3-hydroxyl through a chain of hydrogen bonds. In this configuration, the protonation of the 1-oxide oxygen is disfavored, and protonation could nevertheless result in the deprotonation of the 3-hydroxyl group, thereby regenerating 2-[(1R,6R)-6-isopropenyl-3-methylcyclohex-2-en-1-yl]-3-hydroxy-5-pentylphenolate. Specifically, the protonation of the 1-oxide oxygen could deprotonate a bound water (FIG. 1, fourth grey water molecule from the left), which could deprotonate a second bound water (FIG. 1, third grey water molecule from the left), which could deprotonate a third bound water (FIG. 1, second grey water molecule from the left), which could deprotonate a fourth bound water (FIG. 1, first grey water molecule from the left), which could deprotonate the 3-hydroxyl group, thereby regenerating 2-[(1R,6R)-6-isopropenyl-3-methylcyclohex-2-en-1-yl]-3-hydroxy-5-pentylphenolate. Each of these four, bound waters displays near-ideal bond lengths and bond geometries in the model depicted in FIG. 1, which suggests that this configuration and similar configurations contribute to the unexpectedly surprising stability of 2-[(1R,6R)-6-isopropenyl-3-methylcyclohex-2-en-1-yl]-3-hydroxy-5-pentylphenolate in water at a pH ranging from 8 to 10.

What is claimed is:

1. A liquid composition, comprising 2-[(1R,6R)-6-isopropenyl-3-methylcyclohex-2-en-1-yl]-3-hydroxy-5-pentylphenolate, 2-[(1R,6R)-6-isopropenyl-3-methylcyclohex-2-en-1-yl]-5-pentylbenzene-1,3-diol, water, and one or more of sodium ion ($Na^+$), potassium ion ($K^+$), calcium ion ($Ca^{2+}$), magnesium ion ($Mg^{2+}$), chloride ion ($Cl^-$), sulfate ($SO_4^{2-}$), bicarbonate ($HCO_3^-$), and carbonate ($CO_3^{2-}$) wherein the 2-[(1R,6R)-6-isopropenyl-3-methylcyclohex-2-en-1-yl]-3-hydroxy-5-pentylphenolate is dissolved in the water; and wherein the liquid composition comprises the 2-[(1R,6R)-6-isopropenyl-3-methylcyclohex-2-en-1-yl]-3-hydroxy-5-pentylphenolate and the 2-[(1R,6R)-6-isopropenyl-3-methylcyclohex-2-en-1-yl]-5-pentylbenzene-1,3-diol at a molar ratio of 1:10 to 10,000:1.

2. A composition, comprising 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1:10 to 10,000:1, and further comprising one or more of sodium ion ($Na^+$), potassium ion ($K^+$), calcium ion ($Ca^{2+}$), magnesium ion ($Mg^{2+}$), chloride ion ($Cl^-$), sulfate ($SO_4^{2-}$), bicarbonate ($HCO_3^-$), and carbonate ($CO_3^{2-}$).

3. The composition of claim 2, wherein the composition is a liquid, the composition has a pH, and the pH of the composition is 7 to 13.

4. The composition of claim 3, wherein the pH of the composition is 8 to 10.

5. The composition of claim 2, comprising 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1:1 to 100:1.

6. The composition of claim 2, further comprising water.

7. The composition of claim 6, comprising water at a concentration by weight of 50% to 99.99%.

8. The composition of claim 2, further comprising ethanol.

9. The composition of claim 8, comprising ethanol at a concentration by weight of 50 parts per million to 2%.

10. The composition of claim 8, comprising ethanol at a concentration by weight of 1% to 20%.

11. The composition of claim 8, comprising ethanol at a concentration by weight of 10% to 95%.

12. The composition of claim 2, comprising 2-[(1R,6R)-6-isopropenyl-3-methylcyclohex-2-en-1-yl]-3-hydroxy-5-pentylphenolate at a concentration of 1 milligram per liter to 100 milligrams per liter.

13. The composition of claim 2, comprising 2-[(1R,6R)-6-isopropenyl-3-methylcyclohex-2-en-1-yl]-3-hydroxy-5-pentylphenolate at a concentration of 50 milligrams per liter to 5 grams per liter.

14. The composition of claim 2, comprising 2-[(1R,6R)-6-isopropenyl-3-methylcyclohex-2-en-1-yl]-3-hydroxy-5-pentylphenolate at a concentration of 2 grams per liter to 200 grams per liter.

15. The composition of claim 2, further comprising one or more of caffeine, thiamine, niacin, nicotinamide, riboflavin, pantothenate, sucrose, fructose, glucose, acesulfame, saccharin, stevioside, rebaudioside A, sucralose, tagatose, erythritol, maltitol, xylitol, mannitol, isomalt, and a mogroside.

16. A composition, comprising 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 1:10 to 10,000:1, wherein the composition comprises a solid phase, the solid phase comprises a salt, and the salt comprises 2-[(1R,6R)-6-isopropenyl-3-methylcyclohex-2-en-1-yl]-3-hydroxy-5-pentylphenolate.

17. The composition of claim 16, wherein the salt comprises a cation selected from sodium ion ($Na^+$), potassium ion ($K^+$), calcium ion ($Ca^{2+}$), and magnesium ion ($Mg^{2+}$).

18. A composition, comprising 2-[(1R,6R)-6-isopropenyl-3-methylcyclohex-2-en-1-yl]-3-hydroxy-5-pentylphenolate and 2-[(1R,6R)-6-isopropenyl-3-methylcyclohex-2-en-1-yl]-5-pentylbenzene-1,3-diol at a molar ratio of 10,000:1 to 1,000,000:1, and further comprising one or more of sodium ion ($Na^+$), potassium ion ($K^+$), calcium ion ($Ca^{2+}$), magnesium ion ($Mg^{2+}$), chloride ion ($Cl^-$), sulfate ($SO_4^{2-}$), bicarbonate ($HCO_3^-$), and carbonate ($CO_3^{2-}$).

* * * * *